US011173073B2

(12) United States Patent
MacNaughton et al.

(10) Patent No.: US 11,173,073 B2
(45) Date of Patent: Nov. 16, 2021

(54) MONITORING INCONTINENCE EVENTS

(71) Applicant: MacNaughton Living Trust utd Dec. 30, 2002, Portland, OR (US)

(72) Inventors: Carolyn Reeder MacNaughton, Portland, OR (US); Robert Malcolm David MacNaughton, Portland, OR (US)

(73) Assignee: MacNaughton Living Trust utd Dec. 30, 2002, Portland, OR (US)

( * ) Notice: Subject to any disclaimer, the term of this patent is extended or adjusted under 35 U.S.C. 154(b) by 770 days.

(21) Appl. No.: 15/572,154

(22) PCT Filed: May 20, 2016

(86) PCT No.: PCT/US2016/033590
§ 371 (c)(1),
(2) Date: Nov. 6, 2017

(87) PCT Pub. No.: WO2016/187568
PCT Pub. Date: Nov. 24, 2016

(65) Prior Publication Data
US 2018/0116878 A1 May 3, 2018

Related U.S. Application Data

(60) Provisional application No. 62/164,996, filed on May 21, 2015.

(51) Int. Cl.
*A61F 13/42* (2006.01)
*G16H 10/65* (2018.01)
*G08B 21/20* (2006.01)

(52) U.S. Cl.
CPC .............. *A61F 13/42* (2013.01); *G08B 21/20* (2013.01); *G16H 10/65* (2018.01); *A61F 2013/424* (2013.01)

(58) Field of Classification Search
CPC .... A61F 13/42; A61F 13/44; A61F 2013/424; G16H 10/60; G16H 10/65; G08B 21/20; A61B 5/6808
See application file for complete search history.

(56) References Cited

U.S. PATENT DOCUMENTS 7,586,385 B2 9/2009 Rokhsaz
7,812,731 B2 10/2010 Bunza et al.
(Continued)

FOREIGN PATENT DOCUMENTS

JP 2006296566 11/2006
JP 3168620 6/2011
(Continued)

OTHER PUBLICATIONS

International Search Report and Written Opinion for PCT/US2016/033590, dated Oct. 6, 2016, pp. 1-8.
(Continued)

*Primary Examiner* — Catharine L Anderson
(74) *Attorney, Agent, or Firm* — Klarquist Sparkman, LLP

(57) ABSTRACT

Methods and apparatus are disclosed for monitoring incontinence events using inexpensive sensors coupled to an incontinence brief worn by a patient. In some examples of the disclosed technology, a radio frequency identification (RFID) tag is queried to return a sensor value indicating a level of moisture in an incontinence brief. A mobile device carried by a patient caregiver analyzes the sensor value and provides a display indicating a course of action to take, for example, whether to change the patient's incontinence brief.

19 Claims, 12 Drawing Sheets

(56) References Cited

U.S. PATENT DOCUMENTS

| | | | |
|---|---|---|---|
| 7,977,529 B2* | 7/2011 | Bergman | G06Q 50/22 604/361 |
| 8,081,043 B2 | 12/2011 | Rokhsaz | |
| 8,130,094 B2 | 3/2012 | Lu | |
| 8,196,809 B2* | 6/2012 | Thorstensson | A61F 13/42 235/375 |
| 8,237,572 B2 | 8/2012 | Clement et al. | |
| 8,248,249 B2 | 8/2012 | Clement et al. | |
| 8,502,684 B2 | 8/2013 | Bunza et al. | |
| 8,628,506 B2 | 1/2014 | Ales, III et al. | |
| 8,749,319 B2 | 6/2014 | Rokhsaz et al. | |
| 8,866,624 B2 | 10/2014 | Ales, III et al. | |
| 8,978,452 B2 | 3/2015 | Johnson et al. | |
| 9,931,251 B2* | 4/2018 | Euliano | A61F 13/42 |
| 10,028,701 B2* | 7/2018 | Linton | A61B 5/14507 |
| 10,130,524 B1* | 11/2018 | Lai | G08B 21/20 |
| 2002/0145525 A1 | 10/2002 | Friedman et al. | |
| 2006/0174693 A1 | 8/2006 | Chen et al. | |
| 2008/0300559 A1 | 12/2008 | Gustafson et al. | |
| 2009/0160648 A1 | 6/2009 | Rokhsaz | |
| 2010/0072271 A1 | 3/2010 | Thorstensson | |
| 2011/0291810 A1 | 12/2011 | Rokhsaz et al. | |
| 2012/0268278 A1* | 10/2012 | Lewis | A61B 5/208 340/573.5 |
| 2013/0041334 A1 | 2/2013 | Prioleau et al. | |
| 2013/0123726 A1 | 5/2013 | Yu et al. | |
| 2014/0152442 A1* | 6/2014 | Li | A61F 13/42 340/573.5 |
| 2014/0276504 A1* | 9/2014 | Heil | A61G 7/05 604/361 |
| 2015/0080819 A1* | 3/2015 | Charna | A61F 13/42 604/361 |
| 2016/0008182 A1 | 1/2016 | Prokopuk et al. | |

FOREIGN PATENT DOCUMENTS

| | | | |
|---|---|---|---|
| WO | WO 2014/138204 | 9/2014 | |
| WO | WO-2014137671 A1 * | 9/2014 | A61F 13/42 |

OTHER PUBLICATIONS

RF Micron, "Technology Overview," document dated 2017, downloaded from http://rfmicron.com/overview/ on Oct. 27, 2017.

RF Micron, "RFM2120 Product Brief: Wireless Moisture Sensor," document dated 2016, 2 pages.

* cited by examiner

FIG. 4
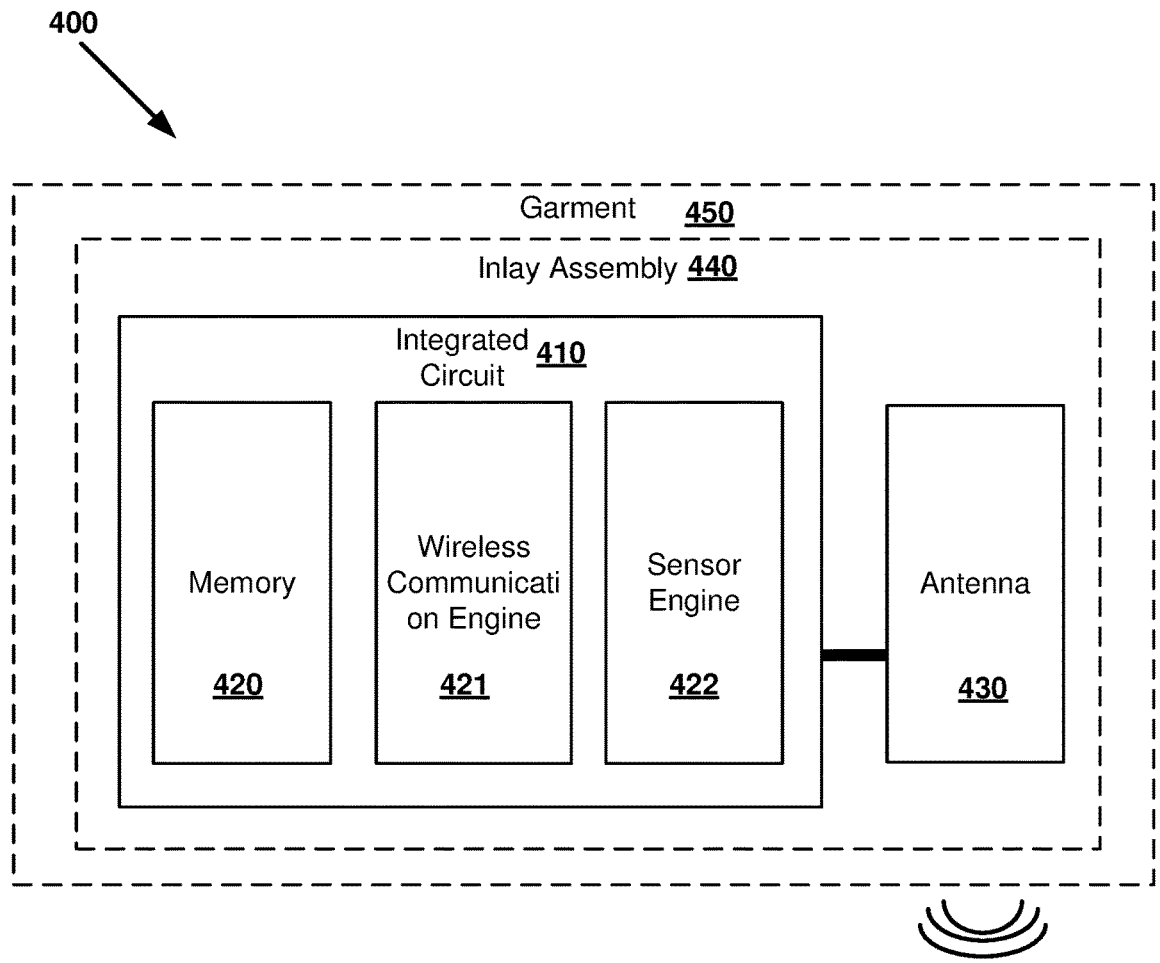
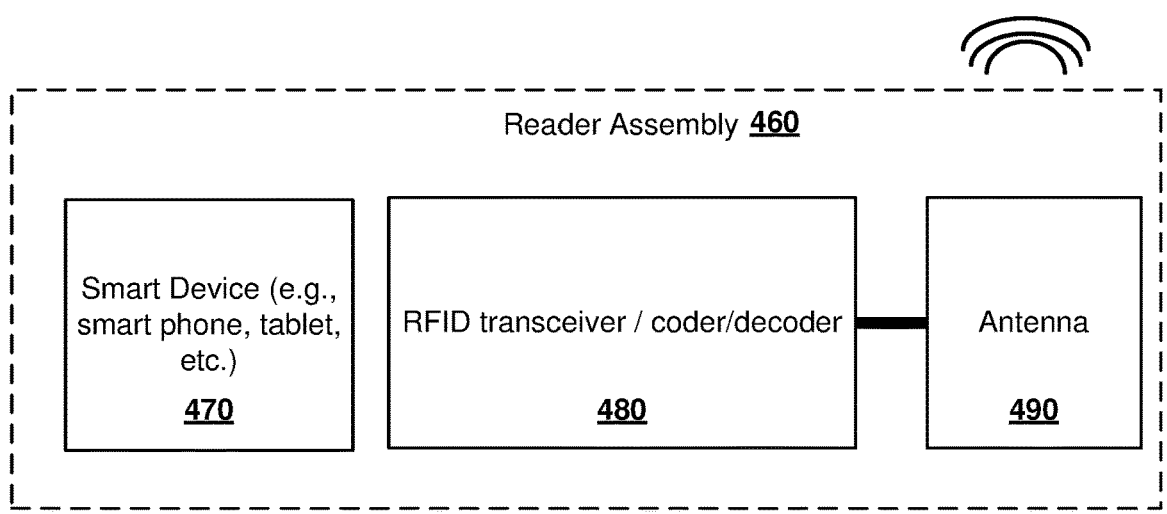

FIG. 12

| Date | Time | Caregiver | Resident | Result | Numeric | Notes | Reminder |
|---|---|---|---|---|---|---|---|
| 1/23/2017 | 13:00 | J. Doe | Resident 1 | Dry | 9 | Resident was resting. Able to determine event without disturbance | 15:00 |

1200

MONITORING INCONTINENCE EVENTS

CROSS REFERENCE TO RELATED APPLICATIONS

This is the U.S. National Stage of International Application No. PCT/US2016/033590, filed May 20, 2016, which was published in English under PCT Article 21(2), which in turn claims the benefit of U.S. Provisional Application No. 62/164,996, filed May 21, 2015. The provisional application is incorporated by reference herein as if set forth fully in its entirety.

BACKGROUND

It is estimated that 25 million Americans are affected by incontinence. The condition affects all ages (however, is most prevalent amongst seniors), all socio-economic levels and both genders. In addition, most sources indicate that estimates of those affected by incontinence may be low as it is a symptom that can be caused by a wide variety of conditions, and in some cases, may only be temporary. Nonetheless, the condition is so prevalent that health professionals deem incontinence as one of the four leading chronic health problems in the U.S.

As a chronic condition, incontinence is projected to increase as the baby boomer population ages. Over the last century, the US population has aged dramatically. In the last 100 years, the U.S. population as a whole has doubled, yet the number of Americans aged 60 or more has increased tenfold. It is also estimated that between 15-30% of Americans aged 60 or more have or will suffer from incontinence. Thus, the challenges created by incontinence will continue to escalate. Incontinence also tends to affect women disproportionately more than men. In fact, 16% of all women experience incontinence by age 75.

Incontinence is particularly problematic in senior-related long-term care (LTC). According to the Department of Health and Human Services, LTC services include a wide range of health, personal care, and supportive services that meet the needs of an older people and other adults whose capacity for self-care is limited because of a chronic illness; injury; physical, cognitive, or mental disability; or other health-related conditions. LTC service providers also include adult living facilities (ALFs), adult day services centers, skilled nursing facilities (SNFs) and similar residential care communities, home health agencies, and hospices; currently accounting for an estimated 5.3 M incontinent residents. The condition is among the most prevalent reasons why seniors are admitted to SNFs and ALFs. It is believed that approximately 50% of all LTC facility admissions are tied to injuries/symptoms related to incontinence. Commensurately, it is estimated that up to 50% of all LTC facility residents suffer from incontinence.

Seniors are often immobile, and if these immobile seniors become incontinent and lose control of the evacuative functions, they may be unable to help themselves or seek help. The urine or feces may stay in place long enough for the elder to develop sores, which can result in sickness, skin breakdown, infections (typically of the urinary tract—UTI), confusion, falls, and the worst case, even death. Incontinence can adversely affect a patient's dignity and can contribute to depression, embarrassment, and social isolation. Long-term care facilities and patients bear the cost of the higher levels of care and emotional/physical strain required to treat these incontinence-related injuries.

The current method of determining whether a person has lost control of his/her evacuative functions requires a caregiver to manually check the bedding and/or brief (often wasting an unused brief). Some seniors may not have the mental capacity to realize if they have had an evacuative function. Others may have the mental facility, but not the physical ability to change on their own. Furthermore, some seniors may find the process awkward or embarrassing, and not signal that a change of brief or bedding is necessary. In addition, some residents have "preferred" caregivers and may wait hours until that caregiver is on shift before alerting facility staff of their need to be changed. From a caregiver perspective, the process may be unappealing, time consuming and challenging. In a facility environment, especially when caregiver coverage ratios are thin, it is these types of tasks that are often delayed or overlooked. Sometimes a resident is left sleeping when a change is needed. The results of this manual system are an inefficient process where briefs are changed when not needed and intrusive checks when unnecessary. This wastes caregiver time and is disruptive for the incontinent individual. Discomfort, bed sore sores, infections, sickness, can result. There is the risk of improper care liability for the facility. Lastly, labor and employee turnover is a major expense for the LTC setting, and for many caregivers, this is the least favorite part of their job and is directly responsible for job dissatisfaction.

Despite the potential size and scope of the incontinence market, incontinence detection devices are not widely available. The most common detection device used in the facility environment is the "blue-stripe" indicator brief. Such briefs use chemical detection means to show a blue stripe when the brief is wet. Although a helpful visual cue for caregivers, this solution still requires the caregiver to disturb the patient/resident in order to view the visible stripe. For example, the caregiver would still need to disrobe the patient/resident at night and use a light in order to check the wetness indicator.

Incontinence affects a large and growing population. It is time consuming and difficult for patient and caregiver to manage well. Yet, if not managed well, there are severe and costly health risks. Accordingly, there is ample opportunity to address the health concerns of incontinence.

SUMMARY

Methods, apparatus, and computer-readable storage media are disclosed for enabling remote detection of incontinence events. In some examples of the disclosed technology, a radio frequency identification (RFID) tag is used. RFID tags are inexpensive, disposable, have indefinite shelf life, and do not require battery power at the source of the sensor. In some examples, an RFID tag including an integrated circuit is affixed to an incontinence brief and a handheld RFID reader to detect when a resident has voided and has a wet brief. When an incontinence event occurs, moisture comes close to the specifically designed RFID tag antenna and "detunes" the tag by altering the permittivity of at least a portion of the area surrounding the antenna. The RFID tag detects a shift in a signal received from a querying RFID reader (e.g., a shift in frequency), encodes the level of detuning detected, and transmits a signal back to the RFID reader indicating a level of detuning measured.

In some examples, the RFID reader is a wearable mobile device that can be carried by a caregiver. When within proximity (e.g., 3-4 feet) of a patient/resident, the caregiver can use the RFID reader to check on the status of the tag affixed to the resident's brief. The RFID reader can be, but is not limited to, a smartphone enabled handheld reader, a Microsoft CE based handheld reader, a Motorola handheld reader, and/or a fixed reader.

This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures.

BRIEF DESCRIPTION OF THE DRAWINGS

FIG. 4 is a block diagram illustrating a number of components that can be used for monitoring incontinence events according to certain examples of the disclosed technology.

FIG. 12 is a table outlining data that can be output using certain examples of the disclosed technology.

DETAILED DESCRIPTION

I. General Considerations

Figure 1:
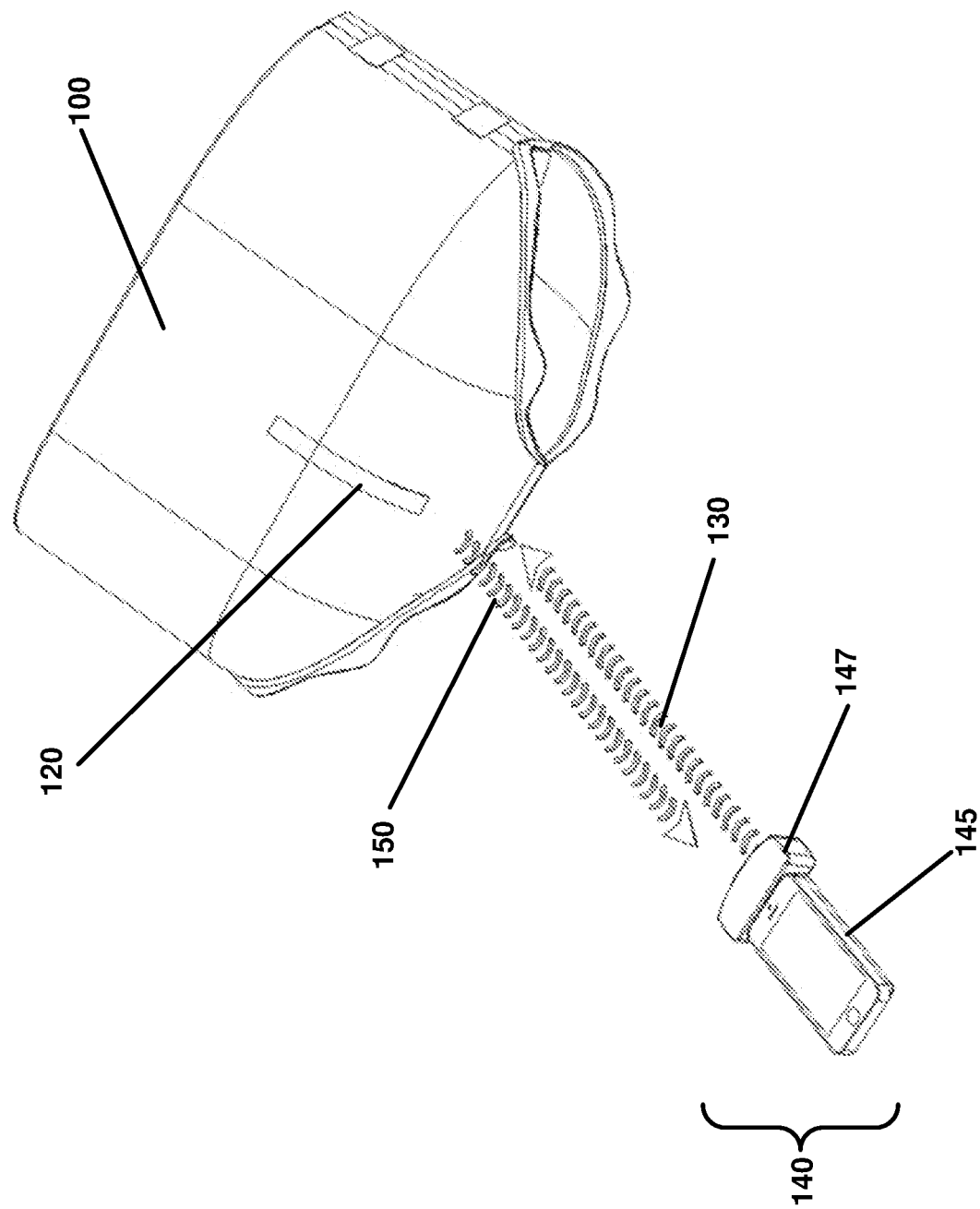
FIG. 1 illustrates a system including an incontinence brief that is attached to a passive RFID assembly and an RFID reader, as can be used in certain examples of the disclosed technology.

This disclosure is set forth in the context of representative embodiments that are not intended to be limiting in any way.

As used in this application the singular forms "a," "an," and "the" include the plural forms unless the context clearly dictates otherwise. Additionally, the term "includes" means "comprises." Further, the term "coupled" encompasses mechanical, electrical, magnetic, optical, as well as other practical ways of coupling or linking items together, and does not exclude the presence of intermediate elements between the coupled items. Furthermore, as used herein, the term "and/or" means any one item or combination of items in the phrase.

The systems, methods, and apparatus described herein should not be construed as being limiting in any way. Instead, this disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed things and methods require that any one or more specific advantages be present or problems be solved. Furthermore, any features or aspects of the disclosed embodiments can be used in various combinations and subcombinations with one another.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed things and methods can be used in conjunction with other things and methods. Additionally, the description sometimes uses terms like "produce," "generate," "display," and "receive," to describe the disclosed methods. These terms are high-level abstractions of the actual operations that are performed. The actual operations that correspond to these terms will vary depending on the particular implementation and are readily discernible by one of ordinary skill in the art.

Theories of operation, scientific principles, or other theoretical descriptions presented herein in reference to the apparatus or methods of this disclosure have been provided for the purposes of better understanding and are not intended to be limiting in scope. The apparatus and methods in the appended claims are not limited to those apparatus and methods that function in the manner described by such theories of operation.

Any of the disclosed methods can be implemented as computer-executable instructions stored on one or more computer-readable media (e.g., non-transitory computer-readable media, such as one or more optical media discs, volatile memory components (such as DRAM or SRAM), or nonvolatile memory components (such as hard drives)) and executed on a computer (e.g., any commercially available computer, including smart phones or other mobile devices that include computing hardware). Any of the computer-executable instructions for implementing the disclosed techniques, as well as any data created and used during implementation of the disclosed embodiments, can be stored on one or more computer-readable media (e.g., non-transitory computer-readable media). The computer-executable instructions can be part of, for example, a dedicated software application, or a software application that is accessed or downloaded via a web browser or other software application (such as a remote computing application). Such software can be executed, for example, on a single local computer (e.g., as an agent executing on any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C, C++, Java, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

II. Example System for Monitoring Incontinence Events

FIG. 1 is a diagram of a system that can be used for monitoring incontinence events. As shown in FIG. 1, an incontinence brief 100 worn by an individual includes a passive RFID assembly 120 attached to the brief. The passive RFID tag assembly 120 includes an antenna and an integrated circuit. The integrated circuit will receive a radio signal 130 transmitted by a reader assembly 140 to the RFID tag assembly 120. In the illustrated example, the reader assembly 140 includes a smartphone device 145 coupled to an RFID transceiver 147. Based on changes in the electric field near the passive RFID tag due to changes in moisture, for example, caused by an incontinence event, the passive RFID assembly 120 detects "detuning" of the signal 130 received from the reader assembly 140. The integrated circuit determines a detuning level and encodes this level as data in a radio signal 150 that is transmitted back to the reader assembly 140.

As shown in FIG. 1, the reader assembly 140 includes a smartphone device 145 coupled to an RFID transceiver 147. It should be noted that other suitable reader assemblies can be used, for example, a special purpose assembly, or in some examples of the disclosed technology, a transceiver is incorporated within the smartphone itself. The passive RFID tag assembly 120 is desirably inexpensive and disposable and can be affixed to the brief when installed on a patient using, for example, an adhesive. In some examples the adhesive is included with the RFID tag assembly 120, such as in a disposable bandage. Because the RFID tag assembly 120 includes a sensor that can detect changes in the signal received from the RFID transceiver 147, accuracy of moisture levels in the incontinence garment can be substantially increased.

The chronically incontinent individual typically wears an incontinence brief (adult diaper) to manage his/her condition. Many individuals who wear incontinence briefs require help from a caregiver to check his/her briefs for the presence of an incontinence event as well as help changing the brief when it has been soiled.

In some examples of the disclosed technology, a user, or more likely a caregiver, affixes an RFID tag to the individual's incontinence brief. In some examples of the disclosed technology, the tags have adhesive on one side, and gauze on the other. In some examples of the disclosed technology, the form factor resembles an adhesive bandage. The backing is removed and an adhesive allows the tag to be placed on the exterior of the brief in the approximate location where a brief will fill with evacuated urine. Alternatively, the tag could be manufactured into the interior of the brief for optimal placement (removes caregiver judgment on placement). The tag could also be designed to be placed on the interior of the brief. The tag can be used with any incontinence brief. It is small and unobtrusive to the individual wearing the brief. The individual puts clothes on and resumes daily activities with the apparatus ready for use.

The caregiver carries a mobile RFID reader (an example of a reader assembly) with him/her. When the caregiver wants to check the condition of an individual's brief (e.g., if it is wet or dry), the caregiver aims the reader antenna in the direction of the individual wearing the RFID tag. In some examples of the disclosed technology, a direct "line of sight" is needed; however, a reading can be taken through clothing, blankets, etc. The caregiver then pushes the start button on the reader to have the reader send a RFID signal to the passive tag. The reading returned gives an indication of whether the antenna is being or has been detuned. The software on the reader then interprets this signal for the caregiver to indicate a wet vs dry condition of the brief. Thus, the caregiver knows if a brief change is needed and will take the appropriate action. Since the disclosed technology will work through blankets and clothing, minimal disruption is needed for the individual.

The reader records the check that was made. Since the handheld reader is directional and a relatively short distance is needed between the tag and reader (2-4 feet), the caregiver can use the reader software to indicate which resident is being scanned and the physical action that was taken for that individual (e.g., was a change made or not). Alternatively a unique identifying code could be encoded on the tag IC to indicate which tag is being read. This data and action recorded can be kept as charting data for the individual patient's care. This data can also be used for management reporting and quality oversight.

III. Example RFID Reader

Figure 2:
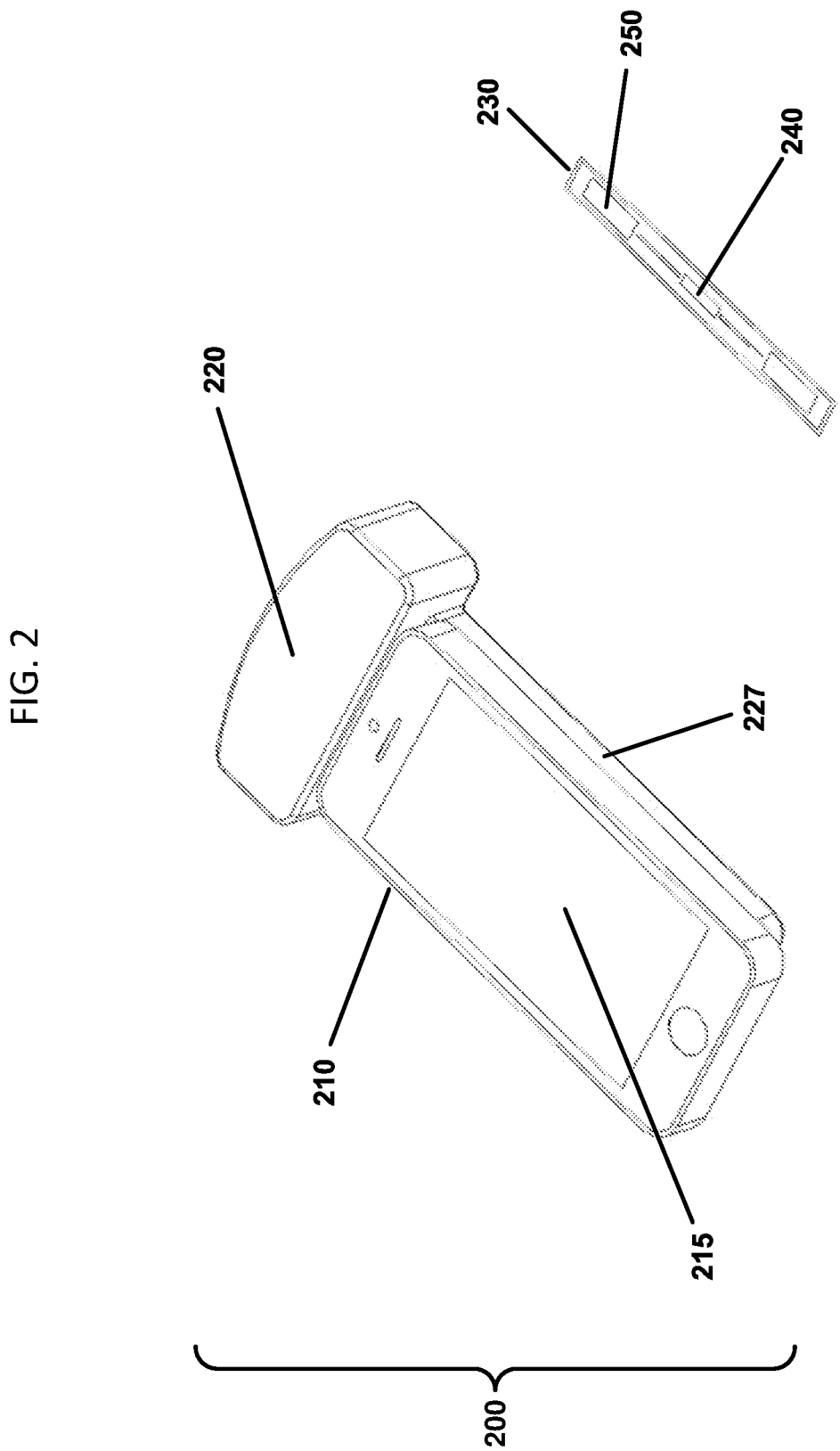
FIG. 2 illustrates a smart phone device coupled to a RFID reader assembly and an RFID tag, as can be used in certain examples of the disclosed technology.

FIG. 2 illustrates an RFID reader assembly 200, as can be implemented in some examples of the disclosed technology. The reader assembly 200 includes a smartphone device 210 which includes a graphical user interface implemented with a touch screen display 215, and is coupled to an RFID reader 220. The RFID reader includes an antenna and a battery 227, which can be used to extend the life of operation of the smartphone device by not drawing power in order to generate RFID signals. In some examples the smartphone can include a touchscreen display, voice recognition, and/or gesture-sensing technologies to enable a user, e.g., a caregiver, to interact and view alerts generated responsive to the RFID tag attached to the patient's garment. Also shown in FIG. 2 is an RFID tag assembly 230 which includes an integrated circuit 240 that is electrically connected to an antenna 250. The antenna 250 is configured such that changes in electric field nearby the RFID tag such as those caused by fluid or other waste being absorbed by the garment manifests as changes in frequency of the signal received by the integrated circuit on the RFID tag assembly 230. Thus, the illustrated system provides an economical system for detecting moisture events in an incontinence garment, without requiring physical inspection of the patient's garment.

Figure 3:
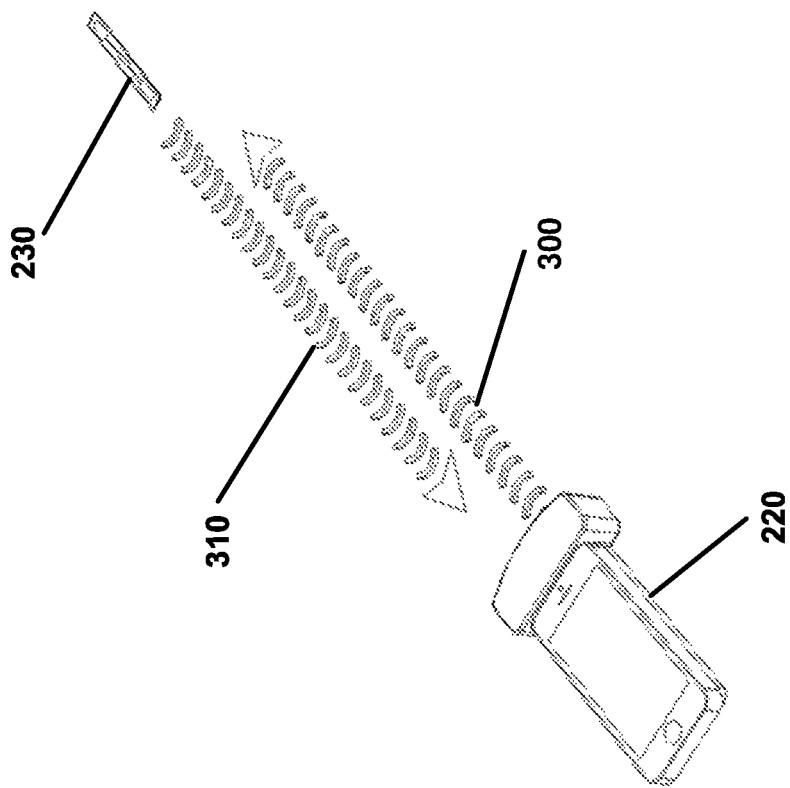
FIG. 3 illustrates an example of an RFID reader signaling to, and receiving data from, an RFID tag assembly.

FIG. 3 illustrates an electromagnetic signal 300 being transmitted from the RFID reader 220 to an RFID tag assembly 230, which transmits a signal 310 back to the reader assembly, as can be performed in some examples of the disclosed technology.

In some examples of the disclosed technology, commercially available handheld RFID readers are used. The caregiver carries the handheld reader with them, and can check on the brief status of the resident at his/her discretion or according to protocol. At this time, the reader is directional, meaning that the reader's antenna needs to be pointed towards the tag it is reading. Currently the readers used can obtain 2-3 feet of read range. This can be enhanced with power output from the reader; however increased power output is directly related to battery life so given current options, a balance is needed. In the current format, slight software modifications are needed for the reader to be able to read the sensor code returned from the IC.

In some examples of the disclosed technology, the reader connects to a smartphone and is enabled through an application on the smartphone. In some examples of the disclosed technology, the smartphone has a custom-built app for it and this is the user interface the caregiver experiences. All data collected through the readings can then be stored, compiled and transferred. In some examples of the disclosed technology, uses all the power available through a smartphone reader. As RFID capability is built into smart devices, there may be a time this additional connection is not necessary. In some examples of the disclosed technology, the reader uses a Windows CE platform and Bluetooth technology to compile and transfer data.

In some examples of the disclosed technology, a fixed RFID reader could be used. These are more powerful as they can connect directly to a plug in the wall, but also are less mobile and more costly at this time. Since the reader needs a line of sight to the tag, the fixed reader is also less flexible for its reading. Yet as reader technology improves, a fixed reader could be constantly monitoring a part of the resident's room such as the doorway, a chair commonly used, or the bed.

FIG. 4 is a block diagram 400 that illustrates a number of components as can be used in some examples of monitoring incontinence events according to the disclosed technology. As shown in FIG. 4, an integrated circuit 410 includes memory 420, a wireless communication engine 421, and a sensor engine 422. The integrated circuit 410 is electrically connected to an antenna 430. The integrated circuit 410 and antenna 430 can be combined into an inlay assembly 440 for convenient use and disposal. The inlay assembly 440 can be produced as a roll of devices, such that a caregiver can detach and attach a single inlay assembly to a garment 450. Alternatively, the inlay assembly 440 can be included with a disposable incontinence garment during manufacture of the garment 450. Regardless of the manner in which the inlay assembly 440 is produced, the assembly is desirably situated near a region of the incontinence garment where liquid resulting from a void event are likely. For example, the position of the inlay assembly can be altered for a male patient versus a female patient. Also shown in FIG. 4 is a reader assembly 460 which includes a smart device 470 such as a smartphone, tablet, or other computing device coupled to an RFID transceiver 480 which includes a coder/decoder for interpreting and encoding data to be sent to and from the garment. The RFID transceiver 480 is also coupled to an antenna 490. Computer executable instructions for implementing the disclosed technologies can be stored in computer-readable storage media located within or accessible to the smart device and/or the memory of the integrated circuit.

IV. Example Computing Environment

Figure 5:
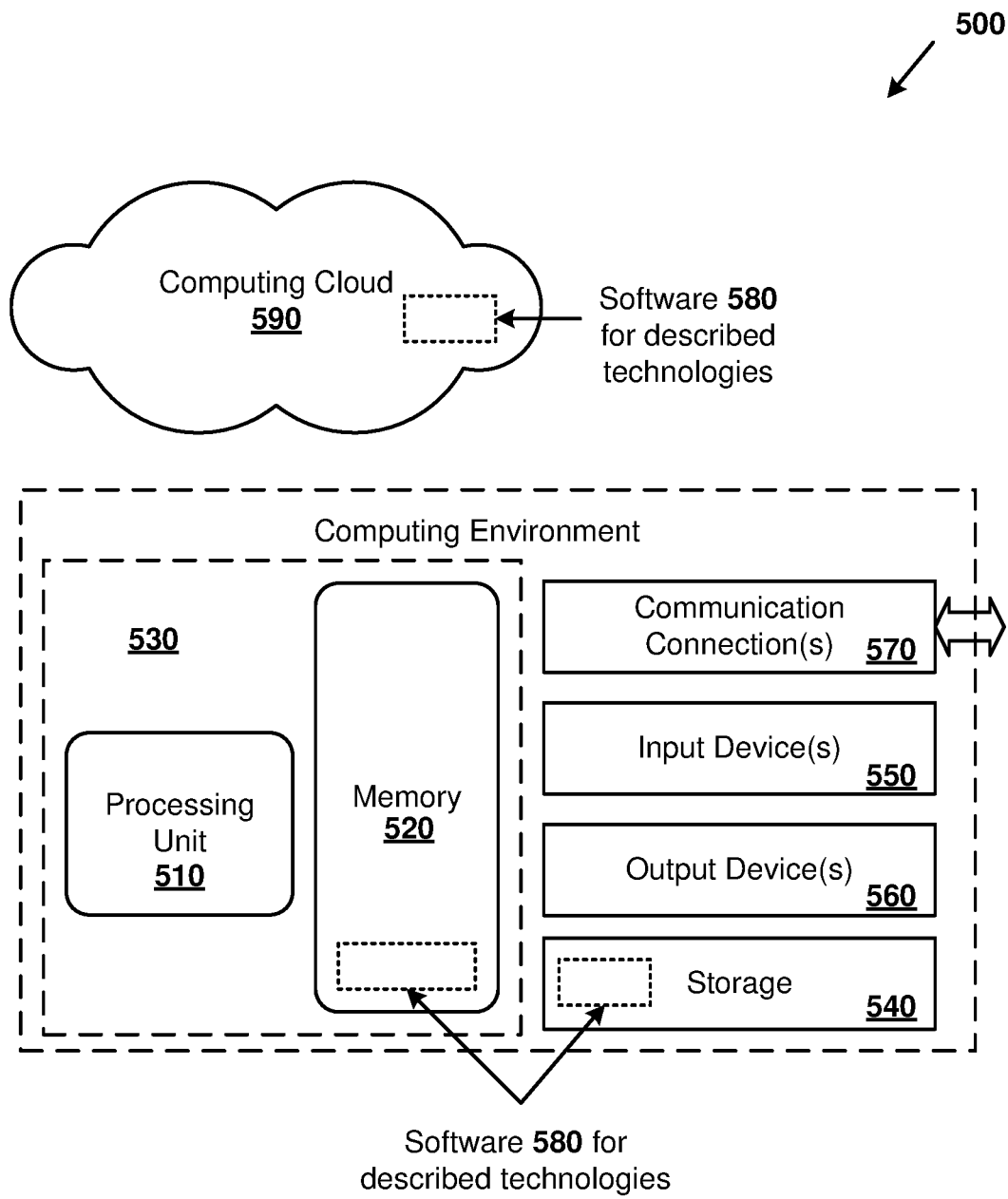
FIG. 5 illustrates a suitable computing environment in which certain examples of the disclosed technology can be implemented.

FIG. 5 illustrates a generalized example of a suitable computing environment 500 in which described embodiments, techniques, and technologies, including reporting agents and monitor servers, can be implemented. For example, the computing environment 500 can implement networked incontinence event monitoring, as described herein.

The computing environment 500 is not intended to suggest any limitation as to scope of use or functionality of the technology, as the technology may be implemented in diverse general-purpose or special-purpose computing environments. For example, the disclosed technology may be implemented with other computer system configurations, including hand held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 5, the computing environment 500 includes at least one central processing unit 510 and memory 520. In FIG. 5, this most basic configuration 530 is included within a dashed line. The central processing unit 510 executes computer-executable instructions and may be a real or a virtual processor. In a multi-processing system, multiple processing units execute computer-executable instructions to increase processing power and as such, multiple processors can be running simultaneously. The memory 520 may be volatile memory (e.g., registers, cache, RAM), non-volatile memory (e.g., ROM, EEPROM, flash memory, etc.), or some combination of the two. The memory 520 stores software 580, images, and video that can, for example, implement the technologies described herein. A computing environment may have additional features. For example, the computing environment 500 includes storage 540, one or more input devices 550, one or more output devices 560, and one or more communication connections 570. An interconnection mechanism (not shown) such as a bus, a controller, or a network, interconnects the components of the computing environment 500. Typically, operating system software (not shown) provides an operating environment for other software executing in the computing environment 500, and coordinates activities of the components of the computing environment 500.

The storage 540 may be removable or non-removable, and includes magnetic disks, magnetic tapes or cassettes, CD-ROMs, CD-RWs, DVDs, or any other medium which can be used to store information and that can be accessed within the computing environment 500. The storage 540 stores instructions for the software 580 and image data, which can implement technologies described herein.

The input device(s) 550 may be a touch input device, such as a keyboard, keypad, mouse, touch screen display, pen, or trackball, a voice input device, a scanning device, or another device, that provides input to the computing environment 500. For audio, the input device(s) 550 may be a sound card or similar device that accepts audio input in analog or digital form, or a CD-ROM reader that provides audio samples to the computing environment 500. The output device(s) 560 may be a display, printer, speaker, CD-writer, or another device that provides output from the computing environment 500.

The communication connection(s) 570 enable communication over a communication medium (e.g., a connecting network) to another computing entity. The communication medium conveys information such as computer-executable instructions, compressed graphics information, video, or other data in a modulated data signal.

Some embodiments of the disclosed methods can be performed using computer-executable instructions implementing all or a portion of the disclosed technology in a computing cloud 590.

Computer-readable media are any available media that can be accessed within a computing environment 500. By way of example, and not limitation, with the computing environment 500, computer-readable media include memory 520 and/or storage 540. As should be readily understood, the term computer-readable storage media includes the media for data storage such as memory 520 and storage 540, and not transmission media such as modulated data signals.

The data captured and recorded by the mobile application is stored locally and via a web-based service, such as a Cloud data storage, which is accessible by facility management through a service-layer. Additionally, this data may integrate into a facility's electronic medical record (EMR) through a secure application programming interface (API). This data may be used for the creation of personalized toileting plans for residents, monitoring and identifying changes in resident incontinence patterns or behaviors, as a reporting capability for resident care decision-makers and long-term care administrators.

V. Example RFID Tag Antenna

The RFID tag has a custom-built antenna designed specifically for the purpose of incontinence detection. The antenna is designed such that the impedance of the antenna can be altered in the presence of moisture, which can also be described as the tag being "detuned." The form of this antenna could be altered to further enhance performance such as extending the antenna to reach to the back of the brief to detect bowel movements. Future iterations could change the shape of the antenna to cover more or less distance on the brief. The antenna shape could also be adapted in the case that the tag is placed on the interior of the brief. In this case, how the antenna is optimized could depend on placement, gender of the wearer, physical shape of the brief, or the absorbent materials used on the interior of the brief. In some examples of the disclosed technology, the tag could also be detuned or disrupted through a physical change to the antenna such as a conductive coating being used as the material for the antenna. In this case if the antenna shape is physically altered, the antenna would be detuned or disrupted. In some examples of the disclosed technology, the antenna can be physically altered in the presence of moisture.

The tags have been created in both copper and aluminum forms and work well. Aluminum has been chosen as the optimal form because of its lower cost, however antennas made from copper or another suitable conductive material can be used. As discussed above, an antenna that is comprised of material/coating that will physically change in the presence of urine is also possible.

The purpose of the antenna remains the same regardless of these variations, and that is to effectively "detune" or negate the passive RFID tag and give a different response to a reader depending on its proximity to urine.

Figure 6:
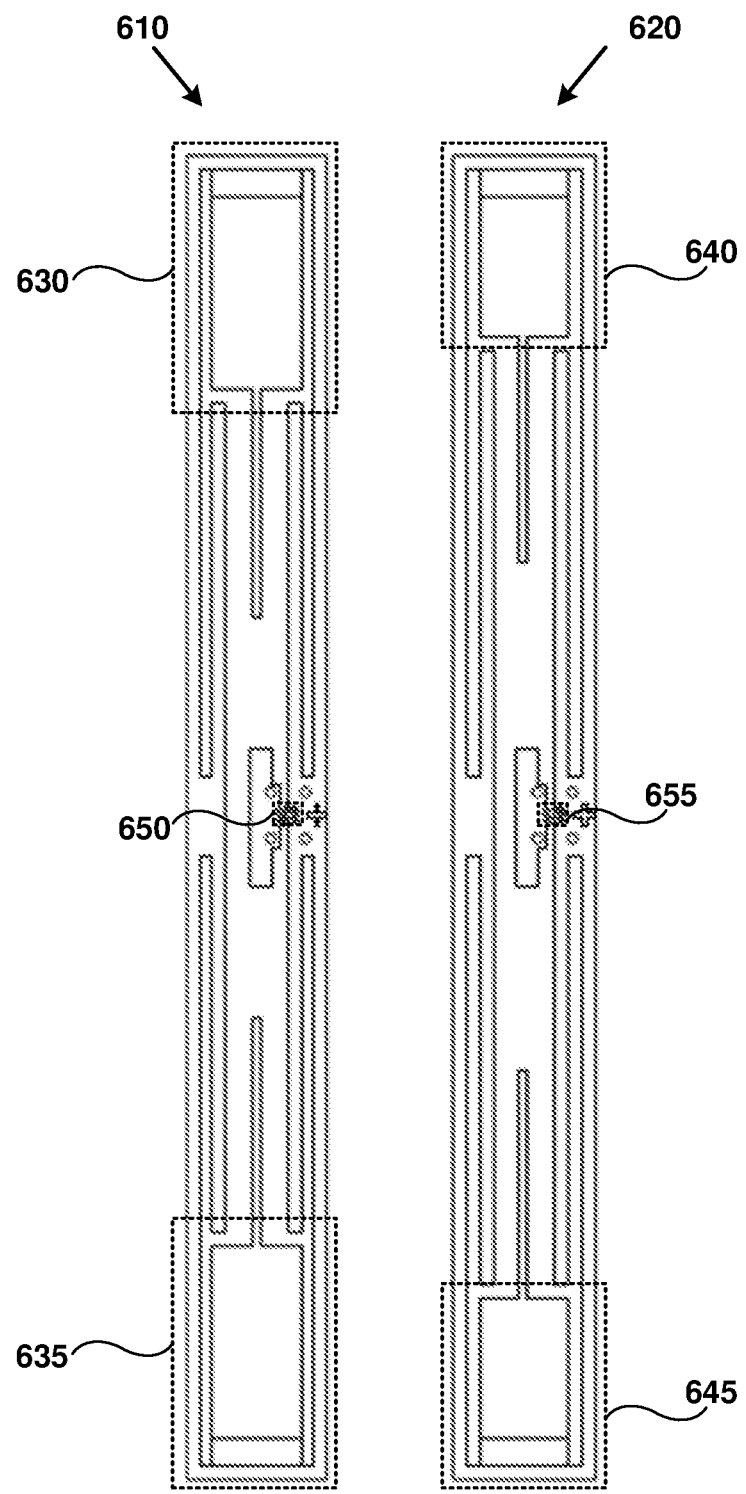
FIG. 6 is a plan view of two RFID antenna assemblies that can be used in certain examples of the disclosed technology.

FIG. 6 illustrates two examples of antennas (610 and 620) suitable for use within an RFID assembly for placement on an incontinence garment. As shown in FIG. 6, each of the antenna designs 610 and 620 is a bi-pole design including a loop on the distal ends of the antenna. The antenna 610 on the left has been designed with larger loops 630 and 635, while the antenna 620 on the right has been designed with smaller loops 640 and 645. Each of the antennas 610 and 620 is designed to be connected to an integrated circuit (650 or 655, respectively) at the lower middle portion of the antenna, thereby forming a bi-pole antenna. As will be readily apparent to one of ordinary skill in the art, the design of the RFID antenna can be modified to suit a particular application and adapted to various RFID reader technologies, including active and passive signaling technologies.

Figure 7:
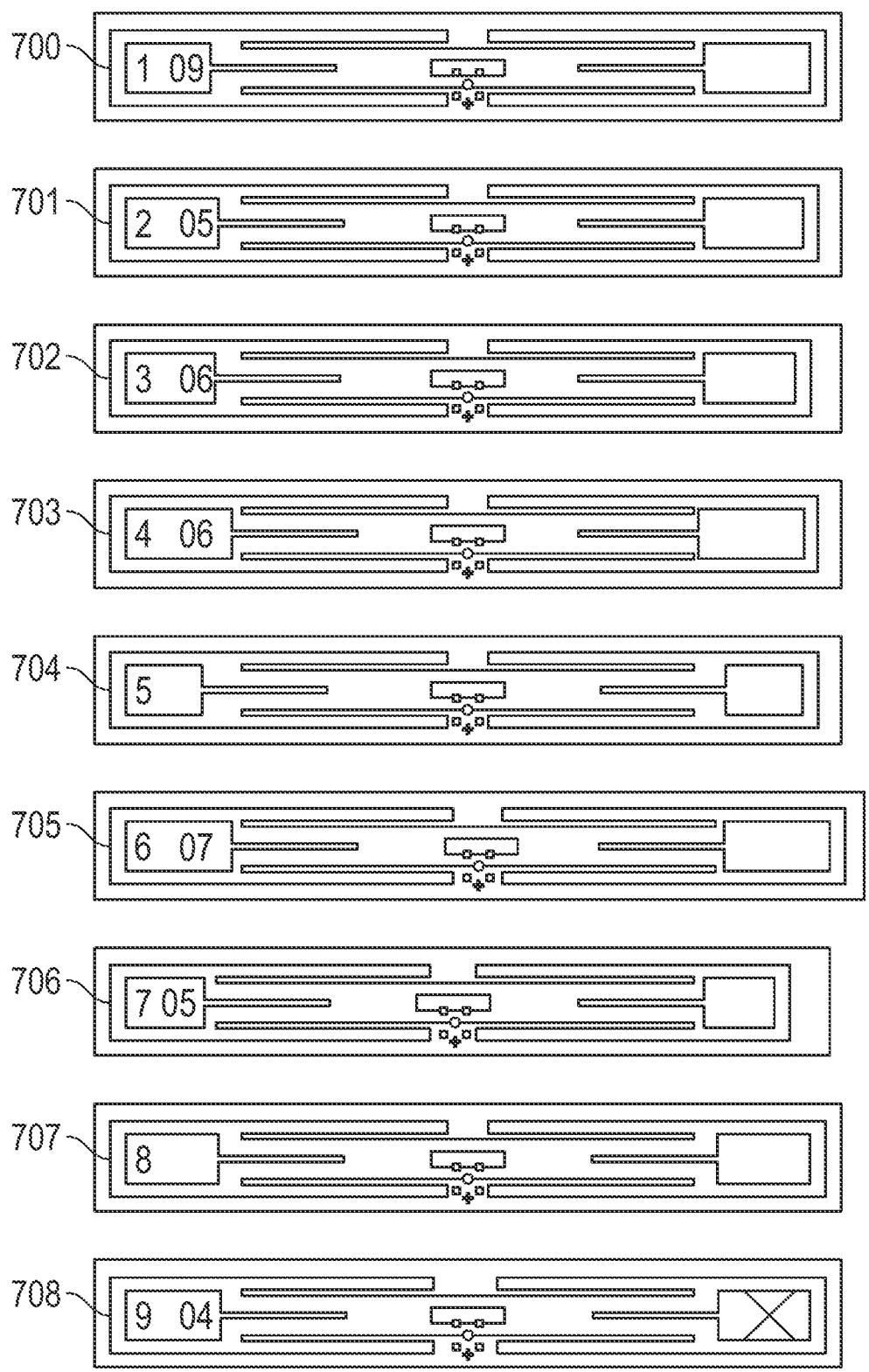
FIG. 7 is a photograph of a number of suitable RFID assemblies that can be used to implement certain examples of the disclosed technology.

FIG. 7 is a photograph of nine different antenna designs (700-708) as can be used in certain examples of the disclosed technology. As shown in FIG. 7, testing by the inventors indicates that the designs numbered 703 and 704 are more favorable in certain implementations. However, it should be understood that any suitable antenna, including those not illustrated in FIG. 7, can be employed.

VI. Example RFID Tag Integrated Circuit (IC)

The tag antenna is managed by an integrated circuit located on the tag. When a reader sends a signal to the tag, it is the IC that answers back. A more standard IC answers back to a reader typically with an identifier that has been encoded, essentially telling the remote reader what it is through the code. This is how RFID is typically used for inventory purposes.

In some examples of the disclosed technology, the IC answers back with a reading of how hard that IC is working given how the antenna is being "detuned." This has been termed a "sensor code" which is essentially an arbitrary scale created from, for example, 1-30 that can indicate the amount of "detuning" the antenna is experiencing. In some examples of the disclosed technology, a sensor code of 1-14 indicates a dry brief and 15-30 indicates a wet brief. Although a sensor code is returned to a reader, the interface on the reader is adjusted to let the caregiver know whether a wet vs dry condition exists, thus the code is translated into an action for the caregiver.

In some examples of the disclosed technology, the amount a tag has been detuned is considered a proxy for the amount of void that has taken place. In the some examples, a reader looks for a binary indication, however, more complex diagnostics can also be considered (e.g., dehydration, change in urinary pattern), in which the amount of detuning could become very useful information. The amount of detuning could determine the content of the urine, highlighting the condition of the individual, e.g., infection. Furthermore, detuning to a marker that is remembered and triggered such as temperature could also be powerful information to indicate a condition of the individual.

Figure 8:
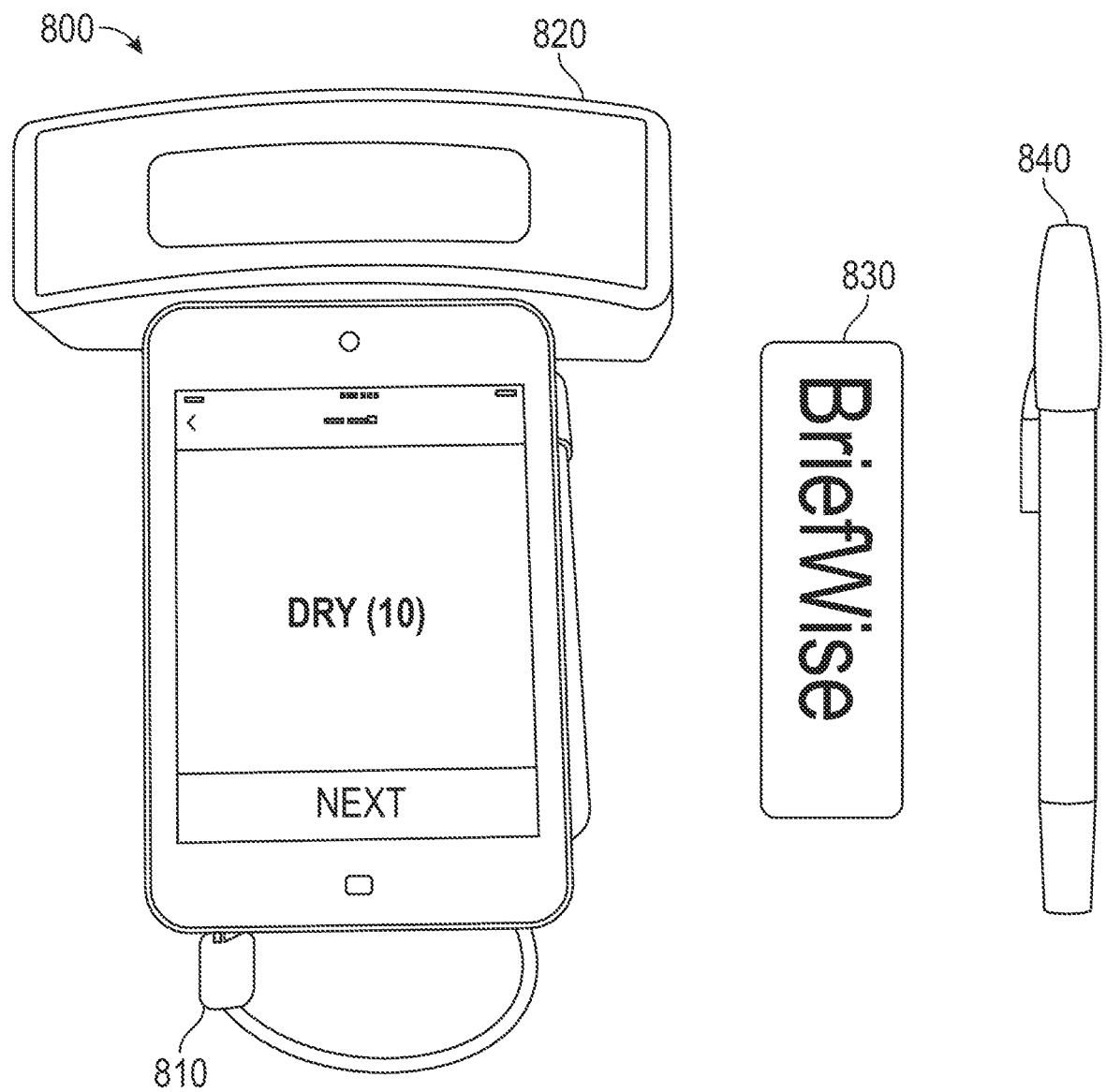
FIG. 8 is a photograph of a mobile device coupled to an RFID reader that can be used in certain examples of the disclosed technology.

FIG. 8 is a photograph 800 of a smartphone device 810 coupled to a reader 820, an RFID tag assembly 830, including adhesive backing, and a pen 840 (for scale). The smartphone device 810 is shown displaying a graphical user interface, which can be used to implement applications and accessed by a caregiver to interact with an RFID tag assembly assigned on a patient's garment. As shown in FIG. 8, the smartphone device 810 has used a graphical user interface (GUI) of a software application with the reader 820 to submit a query to an RFID tag assembly attached to a garment. Responsive to detecting a moisture level using detuning methods as disclosed herein, the RFID tag assembly returns a sensor code value of ten (10), which the smartphone device in turn interprets as a dry condition. The software application displays the condition as "DRY" on a green background, along with the sensor code value. The smartphone application GUI also is displaying a touch screen display button labeled "Start," which can be used to initiate the query sequence again. On the query is transmitted and a sensor code detected, the GUI will display the new sensor code value and also update the interpretation of the moisture level (e.g., by displaying "WET" or "CHANGE"). In the event that a sensor code is not detected, the GUI can display an error message or query the user to initiate another attempt. In other examples, additional information can be displayed, such as an indication of the patient's temperature, an infection condition, dehydration, or other suitable information. In some examples, the smartphone device transmits the sensor code to a server for analysis and storage. In some examples, the smartphone device receives an interpretation of the moisture level and/or historical moisture and garment change data, which can be displayed using the touch screen display of the smartphone.

Figure 9:
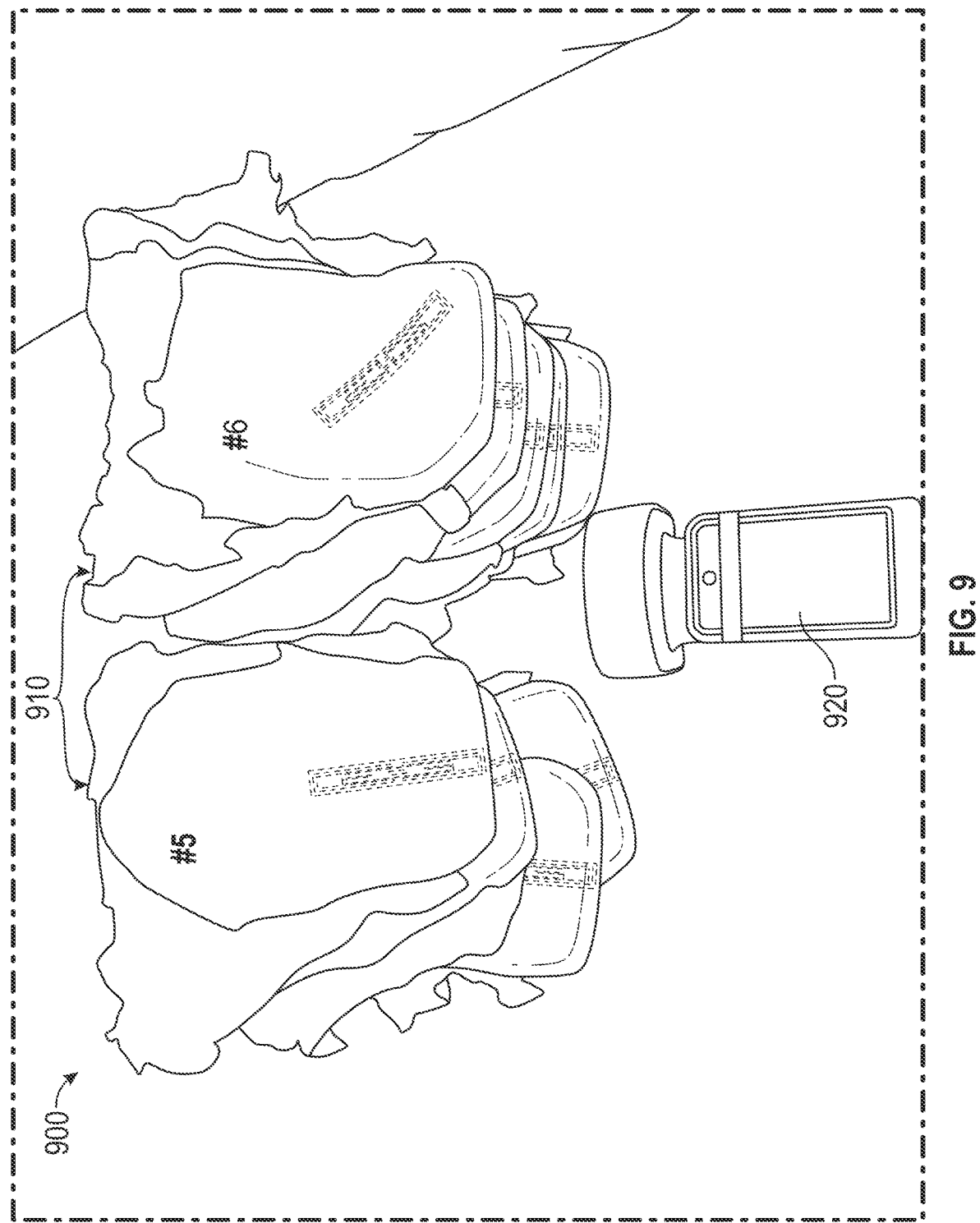
FIG. 9 is a photograph of a number of incontinence garments coupled to an RFID antenna and a smart device, as can be used in certain examples of the disclosed technology.

FIG. 9 is a photograph 900 illustrating a number of incontinence garments 910 that have an RFID tag assembly attached to the garments. Also shown in FIG. 9 is a smartphone device 920 in communication with an RFID tag attached to one of the garments.

The disclosed technology offers the potential to significantly modernize the way incontinence is managed today. It uniquely offers a disposable, inexpensive technical solution to manage the most basic of human needs. It can offer a massive increase in quality of care/dignity to individuals, assist caregivers manage a difficult condition, and offer cost savings/risk mitigation to LTC facilities.

The benefits to the patient/resident, caregiver, and facility are enormous. From a resident perspective, he/she would not unnecessarily suffer the distress and discomfort of wet/fecal conditions. Furthermore, the resident would not be subjected to needless incontinence checks throughout the day and night. More significantly, quick detection of an incontinence event would mitigate more serious injuries such as sores, skin breakdown, and other infections. Caregivers would only be required to quickly react to incontinence events. They can dispose of the sensor (along with the brief) after use. There would be no need to continually check on and disturb the residents, making them feel uncomfortable or embarrassed and wasting an unused brief. Facilities would be able to routinely monitor, assess and record incontinence events (chart) without wasting briefs or caregiver time. More importantly, facilities would be able to reduce, or even potentially eliminate care costs related to incontinence-related injuries. As health care reforms continue to push accountability for cost to providers, the savings potential, and risk reduction for facilities is enormous.

In some examples of the disclosed technology, an RFID integrated circuit is configured to keep a tag functional when near moisture (e.g., when the impedance of the antenna is altered). In this use case, the RFID integrated circuit detects when the RFID integrated circuit is attempting to retune itself, e.g., when the IC is adjusting its receiving antenna impedance to maintain a reading, thereby indicating the presence of moisture. When the RFID reader sends a signal to the passive RFID tag, the response given from the tag enables the reader to tell whether that tag is in the presence of moisture or not, thus whether the brief is wet or dry.

In some examples of the disclosed technology, a RFMicron technology Magnus® S family of products provides a passive, wireless, single-chip sensor solution that can be used to implement disclosed methods and apparatus. In some examples, an integrated circuit automatically adjusts the input impedance of the IC to optimally tune the tag to varying frequencies and environmental conditions. In some examples, a self-tuning circuit produces a 5-bit sensor code using a standard Electronic Product Code (EPC) Gen2 READ command. Thus, the sensor code provides a direct measure of the antenna's impedance. Based on the chosen antenna design and the effect of the environment on the impedance, changes in the sensor code indicate a change in the environment.

On-chip Received Signal Strength Indication (RSSI), which indicates the strength of the signal sent from the sensor to an RFID reader, can also be employed by an integrated circuit in some examples of the disclosed technology. In some examples, the On-Chip RSSI is a 5-bit digital output that can be read by the reader using standard EPC Gen2 commands and can be used as a data resource providing a direct measurement of the signal strength seen by the tag. This feature is useful in development, characterization, and system installation to manage the response of large tag deployments. In some examples, the sensor code reading indicating the amount of detuning, and the RSSI signal strength indication can be combined to generate a more accurate measurement of the amount of moisture in the garment.

In some examples of the disclosed technology, electromagnetic signals having frequencies in the range of 860-960 MHz are used to transmit signals between an incontinence garment and a reader.

In some examples of the disclosed technology, a dipole antenna is implemented with a passive UHF inlay equipped with an RFID tag integrated circuit. The sensor inlay offers great performance, and accurately detects and measures moisture levels in the surrounding environment.

Data and charting automation of incontinence events allows for powerful analyses. For the resident, if voiding patterns can be established, proactive toileting practices can be put into place. In addition, any changes to patterns may be used as red flags or leading indicators of more serious health issues (e.g., dehydration or UTI infections). Further, the amount of detuning the antenna experiences may be able to be a proxy for the amount of liquid voided, again perhaps to be used as indicators of health issues.

For the facility, aggregate data monitoring can provide useful management tools. Billing of incontinence supplies to each resident can become automated and enable for one inventory supply rather than inventory held for each resident. Legal protection/risk mitigation, and quality metrics are possible by accurate charting of incontinence brief changes. The data collected also enables caregiver oversight to ensure care protocols are implemented. Correlation of change frequency with health outcomes (e.g., UTIs, skin breakdowns, pressure ulcers) can be monitored.

In some examples of the disclosed technology, once a wet garment event is detected, an additional alert is generated if a new garment is not installed within a predetermined period of time (e.g., 30 minutes). In some examples, there is an additional layer of reporting for the supervisor or customer (e.g., Medicare agency, family of patient). In some examples, an absence of readings is reported after a specified period of time to remind the caregiver to go stand next to the patient (and request a reading). In some examples a quality of care metric is generated and reported to management in lieu of the raw data. In some examples of the disclosed technology, a plurality of readings is averaged and/or thresholded to reduce false positives.

Figure 10:
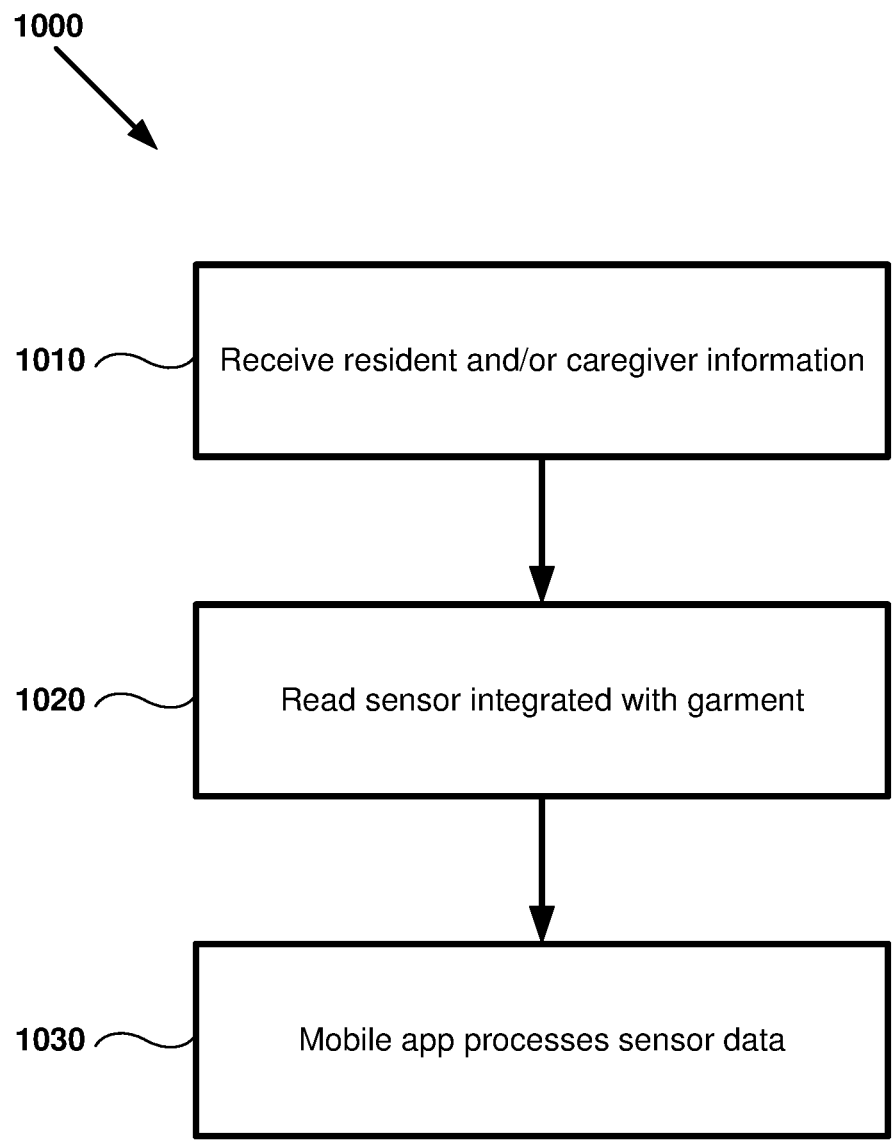
FIG. 10 is a flowchart outlining an example method of processing sensor data received from a garment.

VII. Example Method of Processing Sensor Data,

FIG. 10 is a flowchart 1000 illustrating an example method of reading data from a sensor coupled to a garment, for example an incontinence garment. The example RFID assemblies and mobile devices discussed above can be used to implement the method of FIG. 10.

At process block 1010, information for a resident patient and/or a caregiver is received. For example, the data can include information associating a patient with particular RFID tag identifiers, or associating one or more caregivers with the resident patient.

At process block 1020, a sensor integrated with a garment worn by the resident patient is read. For example, a mobile device coupled to an RFID reader, or an RFID reader embedded in a mobile device itself can send an RF signal to an integrated circuit electrically connected to an antenna. The integrated circuit determines fluctuations in the signal received, calculates the amount of detuning observed at the patient (e.g., due to changes in moisture levels near the antenna), and returns a signal indicating the amount of detuning observed.

At process block 1030, a mobile software application being executed by a processor of the mobile device processes the sensor data produced at process block 1020. For example, the mobile software application can use the data to make a recommendation on whether or not to change a garment worn by the resident patient.

VIII. Example Method of Enhanced Care Using Sensor Data

Figure 11:
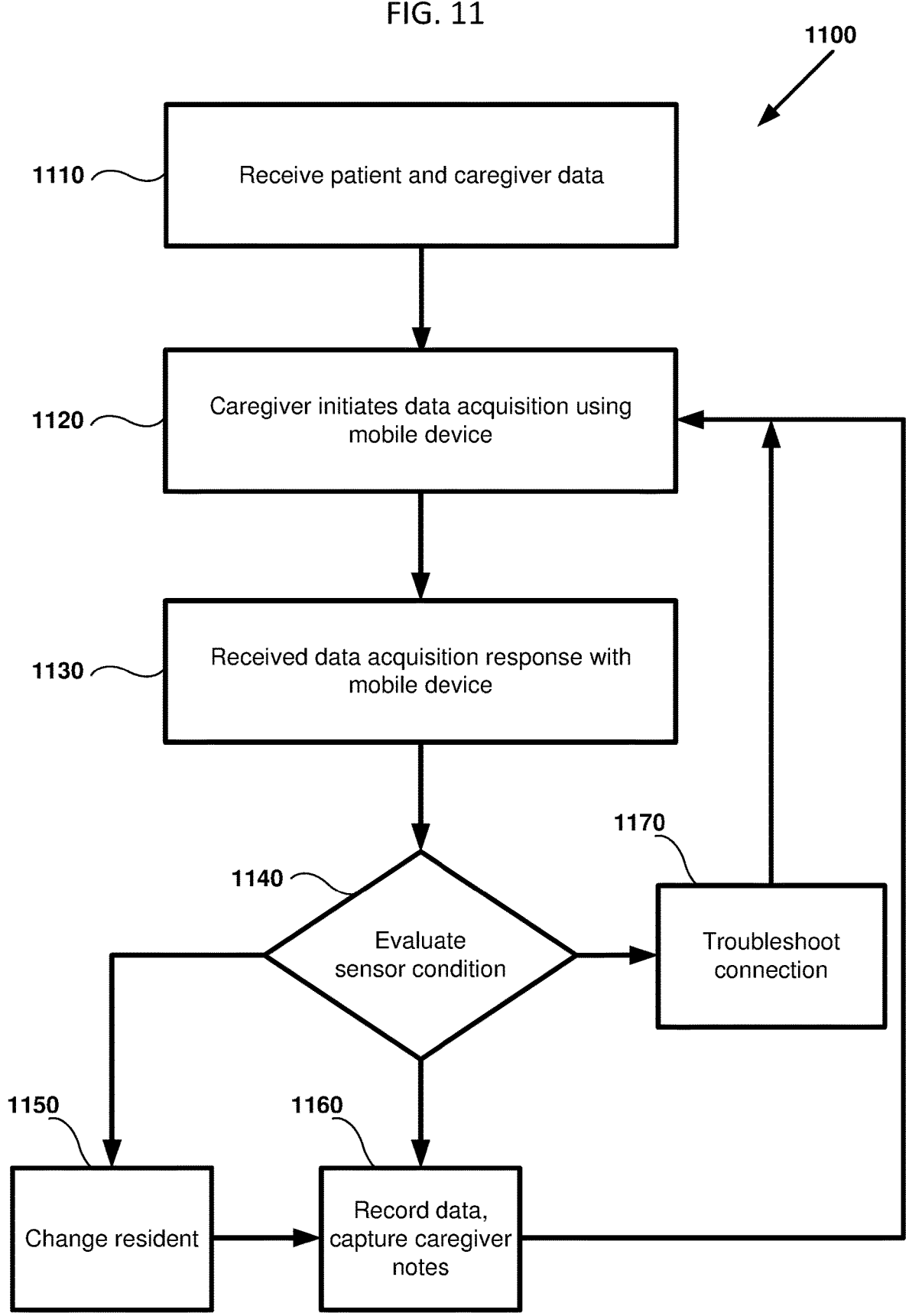
FIG. 11 is a flowchart outlining an example method of evaluating a sensor condition, as can be used in certain examples of the disclosed technology.

FIG. 11 is a flowchart 1100 outlining an example method of evaluating sensor condition data, as can be performed in certain examples of the disclosed technology. For example, the mobile devices and RFID tag assemblies discussed above can be used to implement the method of FIG. 11.

At process block 1110, patient and caregiver data is received. For example, the data can indicate an association between a patient and one or more RFID sensors, and/or an association between a caregiver and locations in a care facility or associations between the caregiver and the patient.

At process block 1120, the caregiver initiates data acquisition using a mobile device. For example, mobile device can use a graphical user interface to display controls that are actuated by the caregiver to initiate data acquisition. For example, as part of normal rounds taking care of a number of different patients, the caregiver can initiate data acquisition when they are within close proximity to the patient.

At process block 1130, data acquisition response data is received by the mobile device. For example, as a result of initiating data acquisition, the mobile device at process block 1120 can send a radio signal that is received by an integrated circuit coupled to a sensor on a garment worn by the patient. The RFID assembly can be positioned such that increased levels of moisture detune the signal received from the mobile device. The integrated circuit in turn determines a moisture level that is encoded as a variable value that is transmitted back to the mobile device. For example, the amount of moisture can be indicated on a scale of 0-30, 0-100, or another suitable range of values. Once the mobile device receives data, the method proceeds to process block 1140.

At process block 1140, the mobile device evaluates the sensor condition based on the received data. If the sensor condition indicates that action should be taken with respect to the patient, then the method proceeds to process block 1150. If the sensor condition indicates that no action is needed with respect to the patient at the current time, then the method proceeds to process block 1160. If the sensor condition indicates that there was a problem acquiring data from the sensor, then the method proceeds to process block 1170.

At process block 1150, the caregiver changes the garment worn by the user, and then uses controls associated with a mobile device to associate a new RFID tag of a new garment worn by the user with records in the computer database associated with the patient. After the resident has been changed and records for the sensor updated, the method proceeds to process block 1160.

At process block 1160, sensor data is recorded and notes entered by the caregiver can optionally be stored along with the patient data. For example, information regarding whether the patient was awake or not, their general condition, and other data can be stored in the database. Further, other data such as time of day and caregiver location can be recorded at the same time. After recording the data and any caregiver notes, the method proceeds to process block 1120, whether the caregiver can initiate data acquisition at a later point in time. Some example data acquisition is initiated by statically placed sensors in a care facility. Thus, as a patient comes into close proximity with the sensors, the data from the patient's garment can be acquired automatically.

At process block 1170, issues with the radio connection between the mobile device and the garment tag are investigated ("troubleshooting"). For example, the caregiver can change position and/or orientation of the RFID reader and reattempt data acquisition.

IX. Example Output Table

FIG. 12 is a table 1200 outlining data that can be output using certain examples of the disclosed technology. As shown, for each reading, a number of data fields are acquired and can be used to determine incontinence events and added to a patient's electronic chart. These fields include data and time that an incontinence sensor was read, name of the caregiver performing the reading, the patient's name, a result expressed as a string (e.g., "Wet" or "Dry"), a numeric value representing a moisture level, notes entered by the caregiver, and a time for sending a reminder to re-check moisture level of the garment using the RFID reader assembly.

X. Example Methods and Apparatus

Exemplary methods as can be practiced in some examples of the disclosed technology, include the following. As will be readily understood to one of ordinary skill in the relevant art, other variations can be performed in combination and sub-combination with each other.

In a first example of the disclosed technology, a caregiver places an RFID tag on the exterior of a resident's incontinence brief (adult diaper) when assisting with changing and dressing. A brief from any manufacturer is suitable. After an elapsed time, the caregiver moves within proximity of resident to be monitored. The caregiver cues the reader to search for a tag by pressing a start "button" displayed with a graphical user interface of the reader. Responsive to the start button being pressed, the reader sends an RF signal from its antenna to search for the RFID tag. The RFID tag (passively or actively) bounces back a reading indicating that it has been found and a signal measurement indicating the amount of detuning the tag antenna is experiencing. Software on the reader averages the return signals to eliminate outlier data and interprets the signal measurement and indicates action to be performed by the caregiver (e.g., wet/change resident or dry/do not disturb resident). If no reading can be detected the software will prompt the caregiver to change position (e.g., Move closer or change angle) and retry by pressing start "button" again. If still no reading is found, the software will prompt the caregiver to conduct a manual check.

In a second example of the disclosed technology, a caregiver places the RFID tag on the exterior of a resident's incontinence brief (adult diaper) when assisting with changing and dressing. The caregiver uses the software interface on the mobile reader to record that the resident has been changed and a new tag employed. After a predefined elapsed time, the caregiver moves within proximity of resident to be monitored. The caregiver uses the software interface to indicate that a check is being made on a particular resident. The caregiver cues the reader to search for a tag by pressing a start "button." The reader sends a signal from its antenna to search for the RFID tag. The tag returns a signal encoding a reading indicating that it has been found and a signal measurement indicating the amount of detuning the tag antenna is experiencing. Software on the reader interprets the signal measurement and indicates the action to be performed by the caregiver (e.g., wet/change resident or dry/do not disturb resident). The reader software records (charts) the check made for a resident and the resulting signal measurement. If no reading is detected the graphical user interface is used to prompt the caregiver to change position (e.g., move closer or change angle) and retry by pressing start "button" again. If still no reading is found, the graphical user interface prompts the caregiver to conduct a manual check.

In a third example of the disclosed technology, a caregiver place the RFID tag on the exterior of a resident's incontinence brief (adult diaper) when assisting with changing and dressing. The caregiver couples his/her smart device (phone, tablet, etc.) of any form (e.g., iPhone or android) with a specialized RFID reader. In other examples, the smart device includes built-in RFID reader functionality. The caregiver uses an application on the smart device to record that the resident has been changed and new tag employed. After a predefined elapsed time period, the caregiver moves within proximity of resident to be monitored. The caregiver uses the smart device application and reader to indicate that a check is being made on a particular resident. The caregiver cues the smart device application to search for a tag by pressing a start "button" on the reader, which sends an RF signal from its antenna to search for the RFID tag. The RFID tag returns a signal indicating that it has been found and a signal measurement indicating the amount of detuning the tag antenna is experiencing. The smart device application analyzes the signal measurement and indicates an action to be performed by the caregiver (e.g., wet/change resident or dry/do not disturb resident). The smart device application records (charts) the check made for a resident, and the resulting signal measurement. If no reading is detected, the software prompts the caregiver to change position (e.g., move closer or change angle) and retry by pressing start "button" again. If still no reading is found, the device prompts the caregiver to conduct a manual check.

In a fourth example of the disclosed technology, a caregiver supervisor allocates uniquely identified tags (EPC code) to a resident and registers the EPC code with the software interface on the reader. The caregiver places the uniquely identified RFID tag on the exterior of a resident's incontinence brief (adult diaper) when, for example, assisting with changing and dressing. The caregiver performs an initial reading of the tag using a smart device reader as described above regarding Examples two or three, such that the smart device reads that a tag is in use. After an elapsed time, the caregiver moves within proximity of resident to be monitored. The caregiver cues the reader to search for a tag by pressing a start "button." The reader sends an RF signal from its antenna to search for the RFID tag. The tag returns a reading indicating that it has been found, its unique EPC code, and a signal measurement indicating the amount of detuning the tag antenna detected. By executing software instruction with the reader, the smart device determines the resident that is being checked, the signal measurement, and indicates the action required by the caregiver (e.g., wet/change resident or dry/do not disturb resident). The software records (charts) the check made for a resident, and the resulting signal measurement. If no reading can be detected the software prompts the caregiver to change position (e.g., move closer or change angle) and retry by pressing start "button" again. If still no reading is found, the software prompts the caregiver to conduct a manual check.

In a fifth example of the disclosed technology, a caregiver places the RFID tag on the exterior of a resident's incontinence brief (adult diaper) when assisting with changing and dressing. The caregiver registers that the RFID tag is newly in use at a central nursing station location. The caregiving facility is equipped with fixed RFID readers placed and aimed at key places for the residents (e.g., doorways, beds, commonly used chairs). The fixed readers periodically (e.g., every 1 minute) transmit an RFID signal to search for tags and their status. The RFID tag returns a reading indicating that it has been found and a signal measurement indicating the amount of detuning the tag antenna is experiencing. Software instructions executed by the reader interprets the signal measurement and notifies caregivers when a change is needed through the nursing station and/or a pager. The software records (charts) the checks made for a resident, and the resulting signal measurement. The tags can be uniquely EPC coded so that the staff knows which resident needs a change or indicates the location of the resident so that the caregiver can then determine which resident has been detected. If still no changes have been made for a particular resident after a certain elapsed time, the software will prompt the caregiver to conduct a manual check and/or make a change.

In a sixth example of the disclosed technology, an RFID tag is printed directly onto an incontinence brief (adult brief) or is built into the interior of a brief. As per the third example above, each brief can be uniquely identified and pre-assigned to a resident. The caregiver uses the software interface on the mobile reader to record that the resident has been changed and a new tag enabled brief employed. After an elapsed time, the caregiver moves within proximity of resident to be monitored. The caregiver uses the software interface to indicate that a check is being made on a particular resident. The caregiver cues the reader to search for a tag by pressing a start "button" with a graphical user interface of a mobile device. The mobile device reader sends a signal from its antenna to search for the RFID tag. The tag returns a reading indicating that it has been found and a signal measurement indicating the amount of detuning the tag antenna observed. Software executing on the reader interprets the signal measurement and indicates the action required by the caregiver (e.g., wet/change resident or dry/do not disturb resident). The software records (charts) the check made for a resident, and the resulting signal measurement. If no reading is detected the device will prompt the caregiver to change position (e.g., move closer or change angle) and retry by pressing start "button" again. If still no reading is found, the device prompts the caregiver to conduct a manual check.

In view of the many possible embodiments to which the principles of the disclosed subject matter may be applied, it should be recognized that the illustrated embodiments are only preferred examples and should not be taken as limiting the scope of the claims to those preferred examples. Rather, the scope of the claimed subject matter is defined by the following claims. We therefore claim as our invention all that comes within the scope of these claims.

We claim:

1. A method comprising:
   with a mobile device coupled to a radio transmitter,
      transmitting a radio frequency (RF) signal comprising an RFID tag read request to an RFID tag electrically connected to an antenna, the RFID tag being attached to an incontinence garment;

responsive to transmitting the read request, receiving an electromagnetic signal comprising a sensor code, the sensor code indicative of a level of moisture in the incontinence garment, the signal being determined at least in part by measuring the antenna's impedance responsive to the RF signal comprising the RFID tag read request signal; and when the sensor code is within predetermined range defined by a predetermined alert value, providing an alert with the mobile device.

2. The method of claim 1, wherein:

the garment is fastened to a patient while the mobile device is in proximity with the garment, the sensor code is based at least in part on an amount of impedance change used to acquire the received signal by the RFID tag; and the method further comprises associating the sensor code with the patient.

3. The method of claim 1, further comprising:

associating an RFID tag unique ID number with a patient when fastening a garment on the patient;

periodically monitoring the patient by transmitting a signal to the RFID tag attached to the patient's garment; and based on the sensor code, storing data in a record for the patient, the sensor code including at least one or more of the following: a patient location, a time, a date, a caregiver identifier, or a moisture level.

4. The method of claim 1, further comprising generating an alert when the sensor code exceeds a predetermined threshold value.

5. The method of claim 1, further comprising:

placing the RFID tag on an exterior surface of a resident's incontinence brief;

after an elapsed time, moving the radio transmitter within proximity of the resident;

initiating a search for a tag by actuating a start button associated with the mobile device;

receiving from the RFID tag a tag indicator and at least one signal measurement indicating an amount of detuning of an antenna of the RFID tag in processing the electromagnetic signal; and with the mobile device, interpreting the at least one signal measurement to indicate an action to be performed by a caregiver.

6. The method of claim 1, further comprising, if no reading is received, then prompting a caregiver to conduct a manual check of the incontinence garment.

7. The method of claim 1, wherein the sensor code indicates at least one of: a wet condition, a dry condition, to change a patient, to not disturb a patient.

8. The method of claim 1, wherein the RFID tag is coupled to an antenna having a loop on distal ends of the antenna.

9. The method of claim 1, wherein the signal is determined by using an integrated circuit on the RFID tag to detect the changes in frequency of the RFID tag read request signal as received at the RFID tag.

10. The method of claim 1, wherein the RFID tag comprises an antenna that is near, but not in contact with, the moisture in the incontinence garment.

11. The method of claim 1, wherein the RFID tag comprises an antenna that is placed on an exterior surface of the incontinence garment in an approximate location where the incontinence garment will fill with evacuated urine.

12. The method of claim 1, wherein the frequency of the RFID tag read request signal is in the range of 860-960 MHz.

13. The method of claim 1, wherein the antenna is attached to the incontinence garment.

14. An apparatus comprising a mobile device, the mobile device comprising:

a processor;

memory coupled to the processor;

an RFID transceiver coupled to the processor;

computer-readable storage media coupled to the processor and storing computer-readable instructions which, when executed by the processor, cause the processor to perform a method, the instructions comprising:

instructions that cause the mobile device to transmit an electromagnetic RFID tag read request signal with the RFID transceiver, the electromagnetic signal comprising an RFID tag read request to an RFID tag, the RFID tag being attached to an incontinence garment;

instructions that cause the mobile device to receive an electromagnetic response signal with the RFID transceiver, the received electromagnetic response signal being sent by the RFID tag responsive to the RFID tag receiving the RFID tag read request signal, the received electromagnetic response signal comprising a sensor code, the sensor code indicative of a level of moisture in the incontinence garment and being determined at least in part by the RFID tag detecting changes in frequency of the RFID tag read request signal; and instructions that cause the mobile device to, when the sensor code is within predetermined range defined by a predetermined alert value, provide an alert.

15. The apparatus of claim 14, wherein:

the sensor code is based at least in part on an amount of impedance change used to acquire the received signal by the RFID tag; and the instructions further comprise instructions that cause the processor to associate the sensor code with a patient in the memory.

16. The apparatus of claim 14, wherein the instructions further comprise:

instructions that cause the processor to associate an RFID tag unique ID number with a patient when fastening a garment on the patient;

instructions that cause the mobile device to periodically monitor the patient by transmitting a signal to the RFID tag attached to the patient's garment; and instructions that cause the processor to based on the sensor code, store data in the memory, the data comprising a record for the patient, and wherein the sensor code includes at least one or more of the following: a patient location, a time, a date, a caregiver identifier, or a moisture level.

17. The apparatus of claim 14, further comprising instructions that cause the mobile device to generate an alert when the sensor code exceeds a predetermined threshold value.

18. The apparatus of claim 14, wherein the RFID tag is affixed to an exterior surface of a resident's incontinence brief, the instructions further comprising:

instructions that cause the mobile device to initiate a search for an RFID tag responsive to a start button associated with the mobile device being actuated;

instructions that cause the mobile device to receive from the RFID tag a tag indicator and at least one signal measurement indicating an amount of detuning of an antenna of the RFID tag in processing the electromagnetic signal; and instructions that cause the mobile device to, based on the at least one signal measurement, indicate an action to be performed by a caregiver.

19. The apparatus of claim 14, wherein the instructions further instructions that cause the mobile device to, responsive to no reading being received, prompt a caregiver to conduct a manual check of the incontinence garment.

* * * * *